(12) United States Patent
Lamoureux et al.

(10) Patent No.: US 7,985,172 B2
(45) Date of Patent: Jul. 26, 2011

(54) AFTER-LOADER DEVICES AND KITS

(75) Inventors: Gary A. Lamoureux, Woodbury, CT (US); Warren W. Johnston, Thomaston, CT (US); Anthony Viselli, Highlands Ranch, CO (US); Paul Walker, Springdale, AR (US); Edward Bleich, Windham, NH (US)

(73) Assignee: Biocompatibles UK Limited, Farnham, Surrey (GB)

( * ) Notice: Subject to any disclaimer, the term of this patent is extended or adjusted under 35 U.S.C. 154(b) by 1098 days.

(21) Appl. No.: 11/741,652

(22) Filed: Apr. 27, 2007

(65) Prior Publication Data

US 2008/0009660 A1    Jan. 10, 2008

Related U.S. Application Data

(63) Continuation-in-part of application No. 11/592,909, filed on Nov. 3, 2006.

(60) Provisional application No. 60/799,161, filed on May 9, 2006, provisional application No. 60/847,834, filed on Sep. 28, 2006.

(51) Int. Cl.
*A61N 5/00* (2006.01)
(52) U.S. Cl. .......................................................... 600/7
(58) Field of Classification Search .................. 600/1–8
See application file for complete search history.

(56) References Cited

U.S. PATENT DOCUMENTS

| | | |
|---|---|---|
| 1,578,945 A | 3/1926 | Withers |
| 2,067,589 A | 1/1937 | Antrim |
| 2,153,889 A | 4/1939 | Frederick |
| 2,575,138 A | 11/1951 | Slaughter |
| 2,668,162 A | 2/1954 | Lowe |
| 2,703,316 A | 3/1955 | Schneider |
| 2,758,987 A | 8/1956 | Salzberg |
| 3,187,752 A | 6/1965 | Glick |
| 3,297,033 A | 1/1967 | Schmitt et al. |
| 3,351,049 A | 11/1967 | Lawrence |
| 3,565,869 A | 2/1971 | De Prospero |
| 3,636,956 A | 1/1972 | Schneider |
| 3,752,630 A | 8/1973 | Takagi |
| 3,811,426 A | 5/1974 | Culver et al. |
| 3,839,297 A | 10/1974 | Wasserman et al. |

(Continued)

FOREIGN PATENT DOCUMENTS

EP    0 030 822 B1    9/1983

(Continued)

OTHER PUBLICATIONS

Alvaro Martinez, et al; "Sterilization of $^{125}$I Seeds Encased in Vicryl Sutures for Permanent Interstitial Implantation"; Intl. J. Radiation Oncology Biol. Phys. vol. 5, pp. 411-413; Pergamen Press Ltd., 1979.

(Continued)

*Primary Examiner* — Samuel Gilbert
(74) *Attorney, Agent, or Firm* — Fliesler Meyer LLP

(57) ABSTRACT

After-loader devices, kits, and methods for using the same are provided. Such after-loader devices are useful for loading implants into hollow needles, especially after the needles are inserted into patient tissue. The after-loader devices can be pre-loaded with implants, before the after-loaders are connected to hubs of hollow needles, or loaded thereafter.

29 Claims, 12 Drawing Sheets

U.S. PATENT DOCUMENTS

| | | |
|---|---|---|
| 3,936,414 A | 2/1976 | Wright et al. |
| 4,052,988 A | 10/1977 | Doddi |
| 4,086,914 A | 5/1978 | Moore |
| 4,141,087 A | 2/1979 | Shalaby et al. |
| 4,167,179 A | 9/1979 | Kirsch |
| 4,402,308 A | 9/1983 | Scott |
| 4,416,659 A | 11/1983 | Simpson et al. |
| 4,441,496 A | 4/1984 | Shalaby et al. |
| 4,452,973 A | 6/1984 | Casey et al. |
| 4,473,670 A | 9/1984 | Kessidis |
| 4,509,506 A | 4/1985 | Windorski et al. |
| 4,510,295 A | 4/1985 | Bezwada |
| 4,612,923 A | 9/1986 | Kronenthal |
| 4,646,741 A | 3/1987 | Smith |
| 4,689,424 A | 8/1987 | Shalaby et al. |
| 4,697,575 A | 10/1987 | Horowitz |
| 4,702,228 A | 10/1987 | Russell et al. |
| 4,741,337 A | 5/1988 | Smith |
| 4,754,745 A | 7/1988 | Horowitz |
| 4,772,287 A | 9/1988 | Ray et al. |
| 4,784,116 A | 11/1988 | Russell, Jr. et al. |
| 4,815,449 A | 3/1989 | Horowitz |
| 4,847,505 A | 7/1989 | Suthanthiran |
| 4,891,165 A | 1/1990 | Suthanthiran |
| 4,916,209 A | 4/1990 | Fung et al. |
| 4,936,823 A | 6/1990 | Colvin et al. |
| 4,946,435 A | 8/1990 | Suthanthiran et al. |
| 5,022,940 A | 6/1991 | Mehoudar |
| 5,242,373 A * | 9/1993 | Scott et al. ................ 600/7 |
| 5,264,540 A | 11/1993 | Cooper et al. |
| 5,339,812 A | 8/1994 | Hardy et al. |
| 5,391,139 A | 2/1995 | Edmundson |
| 5,397,816 A | 3/1995 | Reilley et al. |
| 5,403,576 A | 4/1995 | Lin et al. |
| 5,405,309 A | 4/1995 | Carden, Jr. |
| 5,460,592 A | 10/1995 | Langton et al. |
| 5,521,280 A | 5/1996 | Reilly et al. |
| 5,713,828 A | 2/1998 | Coniglione |
| 5,755,704 A | 5/1998 | Lunn |
| 5,761,877 A | 6/1998 | Quandt |
| 5,833,593 A | 11/1998 | Liprie |
| 5,860,909 A | 1/1999 | Mick et al. |
| 5,928,130 A | 7/1999 | Schmidt |
| 5,938,583 A | 8/1999 | Grimm |
| 6,007,475 A | 12/1999 | Slater et al. |
| 6,010,446 A | 1/2000 | Grimm |
| 6,039,684 A | 3/2000 | Ildstad et al. |
| 6,053,858 A | 4/2000 | Bueche et al. |
| 6,080,099 A | 6/2000 | Slater et al. |
| 6,086,942 A | 7/2000 | Carden et al. |
| 6,099,457 A | 8/2000 | Good |
| 6,132,359 A | 10/2000 | Bolenbaugh |
| 6,132,677 A | 10/2000 | Ohriner |
| 6,132,947 A | 10/2000 | Honan et al. |
| 6,159,143 A | 12/2000 | Lennox |
| 6,163,947 A | 12/2000 | Coniglione |
| 6,200,255 B1 | 3/2001 | Yu |
| 6,200,256 B1 | 3/2001 | Weinberger |
| 6,200,258 B1 | 3/2001 | Slater et al. |
| 6,213,932 B1 | 4/2001 | Schmidt |
| 6,248,057 B1 | 6/2001 | Mavity et al. |
| 6,264,599 B1 | 7/2001 | Slater et al. |
| 6,264,600 B1 | 7/2001 | Grimm |
| 6,273,851 B1 | 8/2001 | Slater et al. |
| 6,283,911 B1 | 9/2001 | Keren |
| 6,312,374 B1 | 11/2001 | von Hoffmann |
| 6,319,190 B1 | 11/2001 | Schmidt et al. |
| 6,327,490 B1 | 12/2001 | Spetz |
| 6,358,195 B1 | 3/2002 | Green et al. |
| 6,360,116 B1 | 3/2002 | Jackson, Jr. et al. |
| 6,387,034 B1 | 5/2002 | Lee |
| 6,398,709 B1 | 6/2002 | Ehr et al. |
| 6,403,916 B1 | 6/2002 | Spooner et al. |
| 6,419,621 B1 | 7/2002 | Sioshansi et al. |
| 6,428,504 B1 | 8/2002 | Riaziat et al. |
| 6,436,026 B1 | 8/2002 | Sioshansi et al. |
| 6,438,401 B1 | 8/2002 | Cheng et al. |
| 6,450,937 B1 | 9/2002 | Mercereau et al. |
| 6,450,938 B1 | 9/2002 | Miller |
| 6,450,939 B1 | 9/2002 | Grimm |
| 6,471,631 B1 | 10/2002 | Slater et al. |
| 6,472,675 B2 | 10/2002 | White et al. |
| 6,474,535 B1 | 11/2002 | Shanks et al. |
| 6,482,178 B1 | 11/2002 | Andrews et al. |
| 6,497,646 B1 | 12/2002 | Candelaria et al. |
| 6,500,109 B2 | 12/2002 | Tokita et al. |
| 6,514,193 B2 | 2/2003 | Kaplan |
| 6,530,875 B1 * | 3/2003 | Taylor et al. ................ 600/7 |
| 6,537,192 B1 | 3/2003 | Elliott et al. |
| 6,537,193 B1 | 3/2003 | Lennox |
| 6,539,247 B2 | 3/2003 | Spetz |
| 6,549,802 B2 | 4/2003 | Thornton |
| 6,554,760 B2 | 4/2003 | Lamoureux et al. |
| 6,561,967 B2 | 5/2003 | Schmidt |
| 6,569,076 B1 | 5/2003 | Larsen et al. |
| 6,572,525 B1 | 6/2003 | Yoshizumi |
| 6,572,527 B2 | 6/2003 | Steele, Sr. et al. |
| 6,575,888 B2 | 6/2003 | Zamora et al. |
| 6,585,633 B2 | 7/2003 | Vitali et al. |
| 6,595,908 B2 | 7/2003 | Loffler et al. |
| 6,599,231 B1 | 7/2003 | Elliot et al. |
| 6,612,976 B2 | 9/2003 | Rosenthal et al. |
| 6,616,593 B1 | 9/2003 | Elliot et al. |
| 6,616,594 B2 | 9/2003 | Fontayne et al. |
| 6,626,817 B2 | 9/2003 | Luth |
| 6,632,176 B2 | 10/2003 | McIntire et al. |
| 6,638,205 B1 | 10/2003 | Chan et al. |
| 6,638,206 B2 | 10/2003 | Green et al. |
| 6,639,237 B2 | 10/2003 | Pedersen et al. |
| 6,648,811 B2 | 11/2003 | Sierocuk et al. |
| 6,656,106 B2 | 12/2003 | Schmidt |
| 6,656,107 B1 | 12/2003 | Pedersen et al. |
| 6,669,621 B2 | 12/2003 | O'Hara et al. |
| 6,669,622 B2 | 12/2003 | Reed et al. |
| 6,679,824 B1 | 1/2004 | Reed et al. |
| 6,682,471 B2 | 1/2004 | Stelle, Sr. et al. |
| 6,689,043 B1 | 2/2004 | McIntire et al. |
| 6,709,381 B2 | 3/2004 | Munro, III |
| 6,716,156 B2 | 4/2004 | Menuhr et al. |
| 6,723,037 B2 | 4/2004 | Hamazaki et al. |
| 6,723,052 B2 | 4/2004 | Mills |
| 6,726,617 B1 * | 4/2004 | Schmidt ................ 600/7 |
| 6,746,661 B2 | 6/2004 | Kaplan |
| 6,749,554 B1 | 6/2004 | Snow et al. |
| 6,752,753 B1 | 6/2004 | Hoskins et al. |
| 6,755,775 B2 | 6/2004 | Kalas et al. |
| 6,761,680 B2 | 7/2004 | Terwilliger et al. |
| 6,786,858 B2 | 9/2004 | Terwilliger et al. |
| 6,790,170 B2 | 9/2004 | Moody et al. |
| 6,800,055 B2 | 10/2004 | Amols et al. |
| 6,805,898 B1 | 10/2004 | Wu et al. |
| 6,820,318 B2 | 11/2004 | Terwilliger et al. |
| 6,837,844 B1 | 1/2005 | Ellard et al. |
| 6,846,283 B2 | 1/2005 | Green et al. |
| 6,905,455 B2 | 6/2005 | Rapach et al. |
| 6,911,000 B2 | 6/2005 | Mick et al. |
| 6,926,657 B1 | 8/2005 | Reed et al. |
| 6,969,344 B2 | 11/2005 | Drobnik et al. |
| 6,989,543 B2 | 1/2006 | Drobnik et al. |
| 7,008,367 B2 | 3/2006 | Visscher et al. |
| 7,060,020 B2 | 6/2006 | Terwilliger et al. |
| 7,074,291 B2 | 7/2006 | Terwilliger et al. |
| 7,083,566 B2 | 8/2006 | Tornes et al. |
| 7,094,198 B2 | 8/2006 | Terwilliger et al. |
| 7,118,523 B2 | 10/2006 | Loffler et al. |
| 7,211,039 B2 | 5/2007 | Lamoureux et al. |
| 7,267,643 B2 | 9/2007 | Koster et al. |
| 7,322,928 B2 | 1/2008 | Reed et al. |
| 7,497,818 B2 | 3/2009 | Terwilliger et al. |
| 7,601,113 B2 | 10/2009 | Lebovic et al. |
| 2001/0008951 A1 * | 7/2001 | Sierocuk et al. ................ 600/7 |
| 2001/0047185 A1 | 11/2001 | Satz |
| 2002/0066824 A1 | 6/2002 | Floyd et al. |
| 2003/0181794 A1 | 9/2003 | Rini et al. |
| 2003/0191355 A1 | 10/2003 | Ferguson |
| 2004/0024453 A1 | 2/2004 | Castillejos |
| 2004/0109823 A1 | 6/2004 | Kaplan |

| | | |
|---|---|---|
| 2004/0158118 A1 | 8/2004 | Drobnik et al. |
| 2004/0225174 A1 | 11/2004 | Fuller et al. |
| 2005/0049490 A1 | 3/2005 | Mills |
| 2005/0261541 A1 | 11/2005 | Henderson et al. |
| 2006/0052654 A1 | 3/2006 | Drobnik et al. |
| 2006/0063960 A1 | 3/2006 | Wissman et al. |
| 2006/0094983 A1 | 5/2006 | Burbank et al. |
| 2006/0121080 A1 | 6/2006 | Lye et al. |
| 2006/0177379 A1 | 8/2006 | Asgari |
| 2007/0224234 A1 | 9/2007 | Steckel et al. |
| 2007/0238983 A1 | 10/2007 | Suthanthiran |

FOREIGN PATENT DOCUMENTS

| | | |
|---|---|---|
| EP | 0 292 630 A | 11/1988 |
| EP | 0 466 681 B1 | 1/1992 |
| EP | 0 668 088 A | 8/1995 |
| EP | 0993 843 A | 4/2000 |
| EP | 1 240 920 A | 9/2002 |
| WO | WO 00/64538 | 2/2000 |
| WO | WO 00/61229 | 10/2000 |
| WO | WO 2008/106586 | 9/2008 |

OTHER PUBLICATIONS

Van't Riet, "Ultrasonically Guided Transperineal Seed Implantation of the Prostate: Modification of the Technique and Qualitative Assessment of Implants", Intl. J. Rad. Onc. Biol. Phys. 24(3): 555-558 (1992).

Middleton et al., "Synthetic Biodegradable Polymers as Medical Devices", Med. Plas. Biomat. (Mar. 1998).

http://investor.mentorcorp.com/news/20010122-32414.cfm, "Mentor Acquires Breakthrough Brachytherapy Technology" (Jan. 25, 2002).

Webster's II New Riverside University Dictionary, p. 191, 1984.

Medi-Physics brochure entitled I-125 Seeds. No. 6711, Medi-Physics, Inc. Arlington Heights Il. 60004, USA; Revised. Oct. 1999, 2 pages.

Medi-Physics brochure entitled I-125 Seeds. No. 7000; Medi-Physics, Inc. Arlington Heights Il. 60004, USA; Revised. Oct. 1999, 2 pages.

Amersham Health; "EchoSeed™"; http://www.amershamhealth-us.com/echoseed/ printed Nov. 19, 2003.

Amersham Health; "Rapid Strand Indications"; Http://www.amershamhealth-us.com/products/index.htp?a=i&i=38; printed Nov. 19, 2003.

Amersham Health; "OncoSeed Indications"; http://www.amershamhealth-us.com/oncoseed/; printed Nov. 19, 2003.

RadioMed: Innovative Products for Radiation, "The Visicoil Advantage . . . for Image Guided Radiation Therapy,"http://www.radiomed.com/visicoil/, at lease as early as Aug. 2003.

Oncura, "RapidStrandR$_x$: The Logical Choice for Improved Dosimetry," Ocura Inc., Plymouth Meeting, PA, Apr. 2005.

Merrick et al., "Seed Fixity in the Prostate/Periprostatic Region Following Brachytherapy," IJROBP vol. 46(1):pp. 215-220 (2000).

Poggi et al., "Marker Seed Migration in Prostate Localization," IJROBP vol. 56(5):pp. 1248-1251 (2003).

Tapen et al., "Reduction of Radioactive Seed Embolization to the Lung Following Prostate Brachtherapy," IJROBP vol. 42(5):pp. 1063-1067 (1998).

Meiller, R., "Advances May Improve Prostate Cancer Treatment," Board of Regents of the University of Wisconsin System, http://www.news.wisc.edu/11899.html, 3 pages (Dec. 1, 2005).

International Search Report for International Application No. PCT/US07/68595.

* cited by examiner

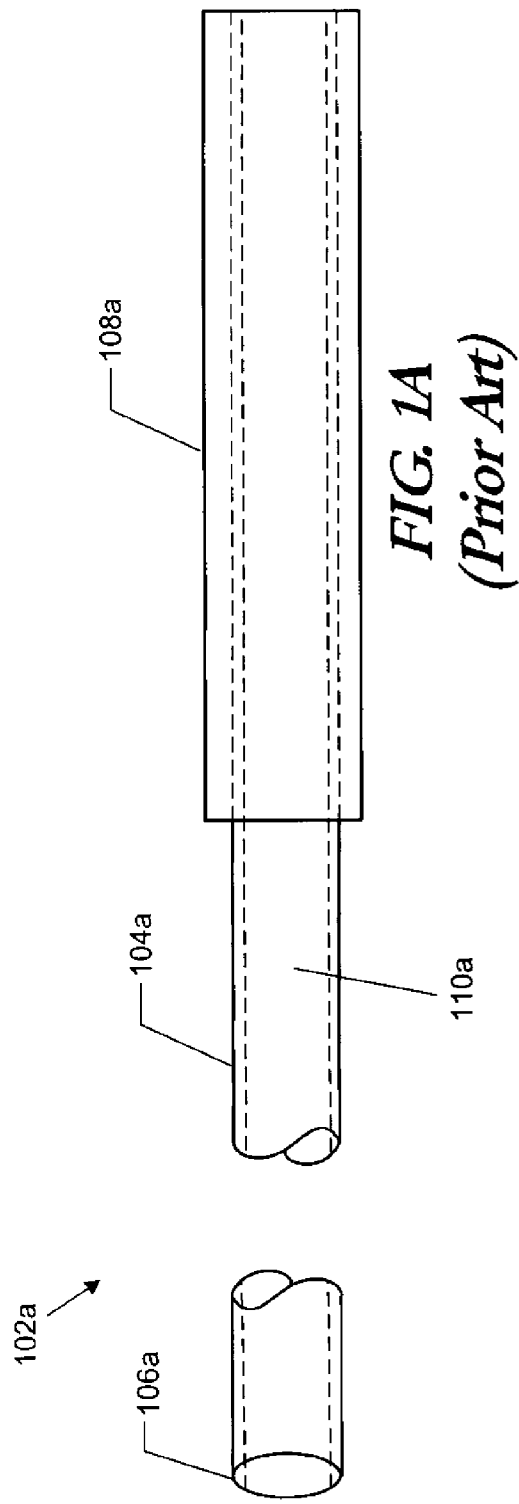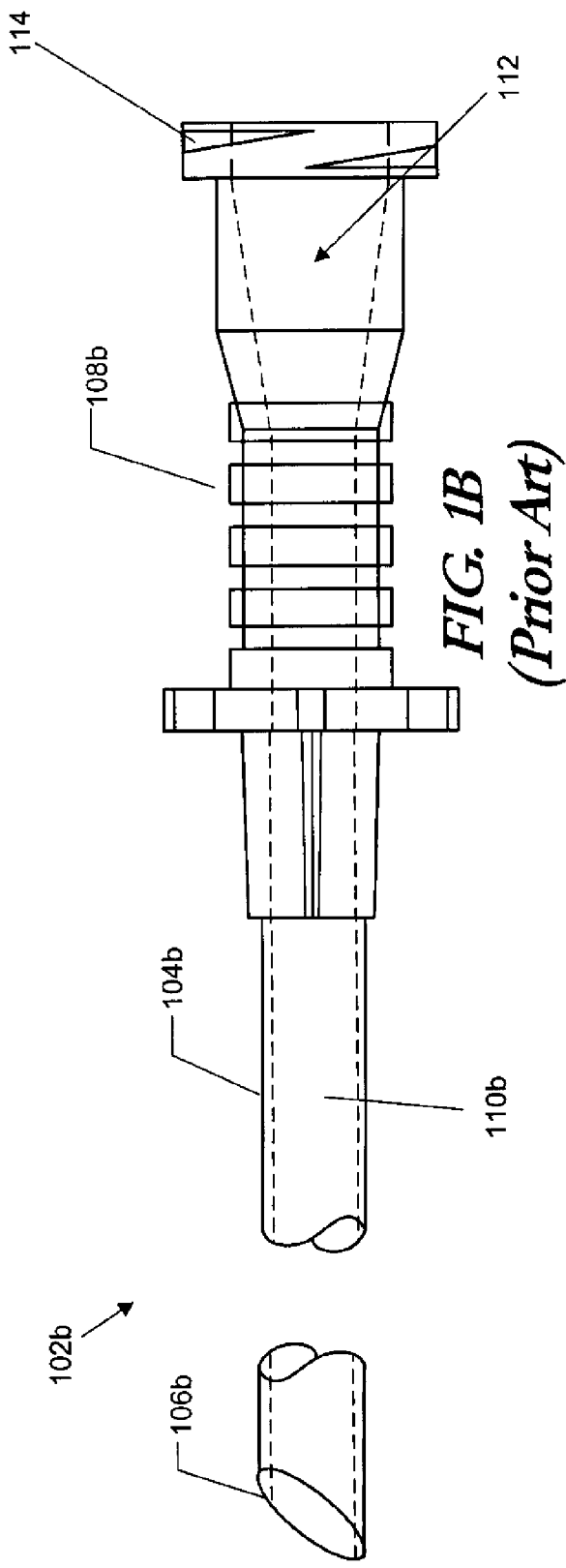

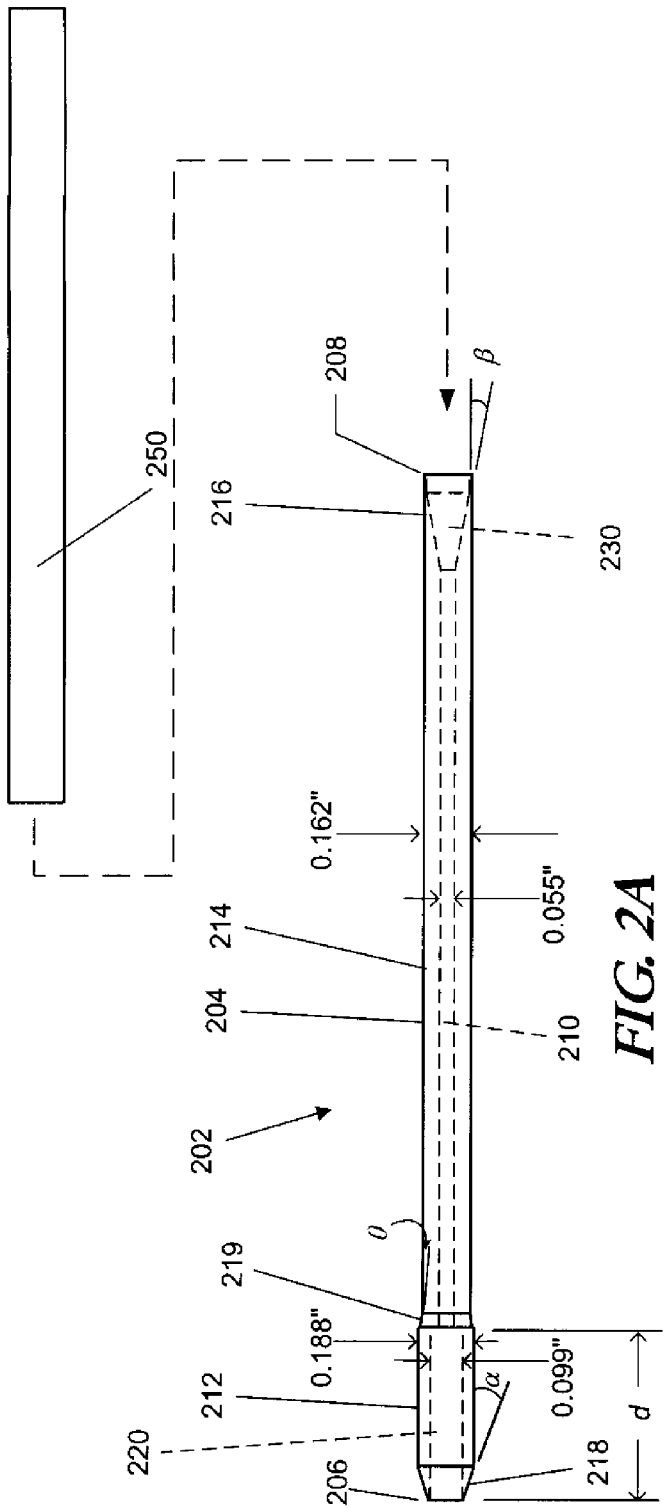
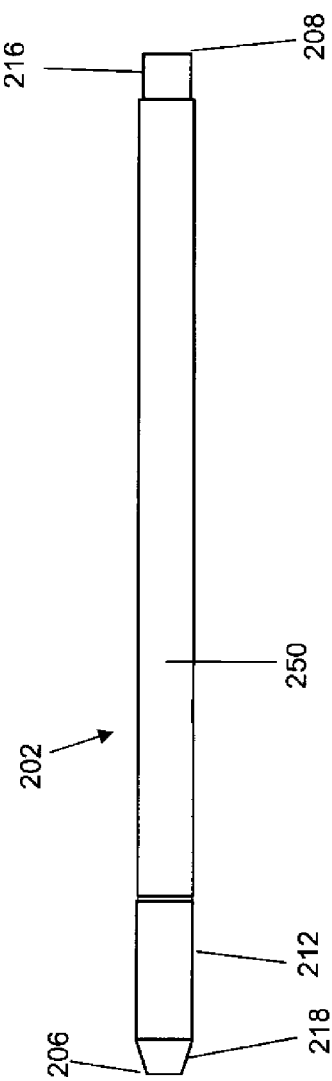
FIG. 2A
FIG. 2B

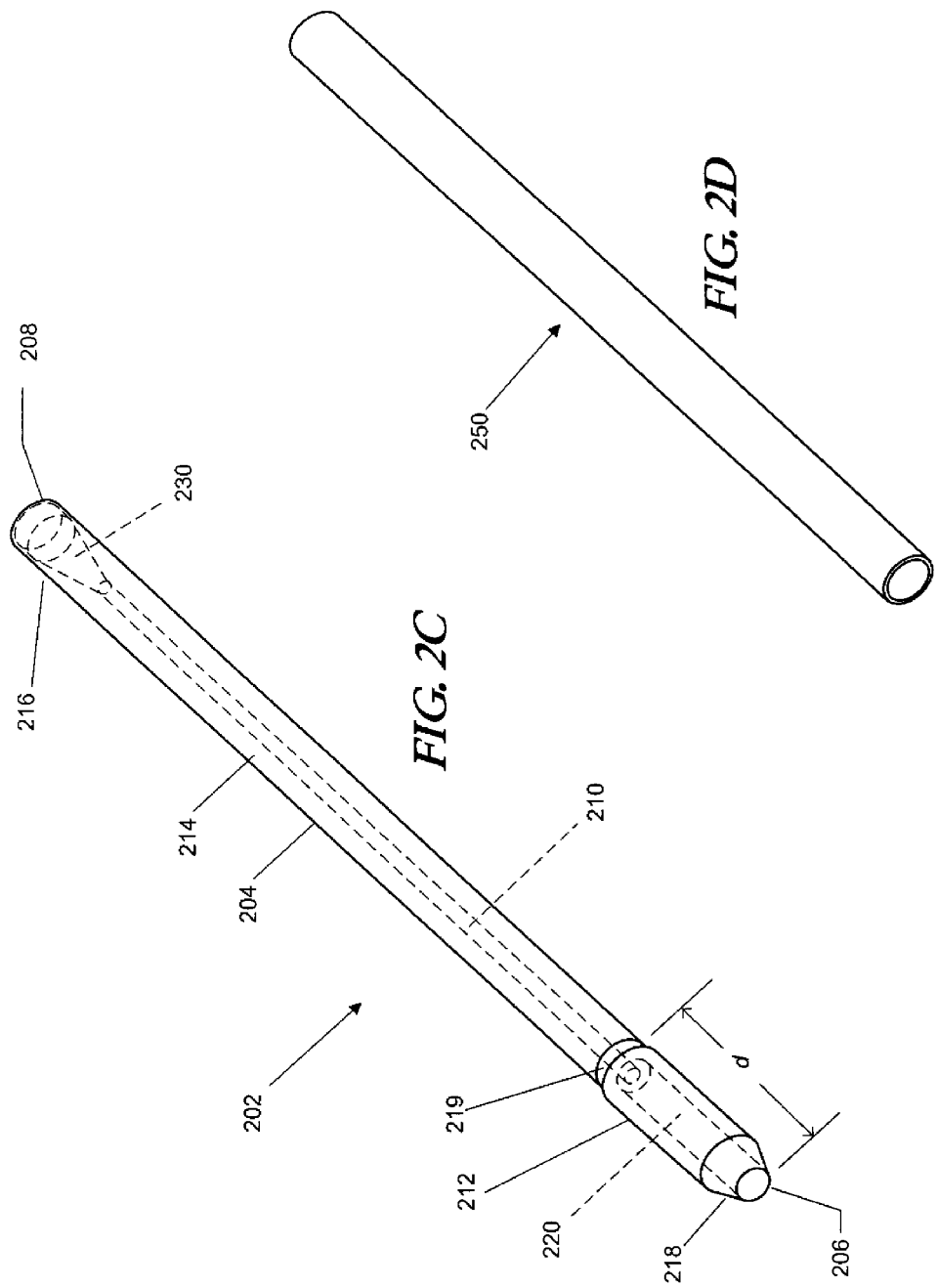

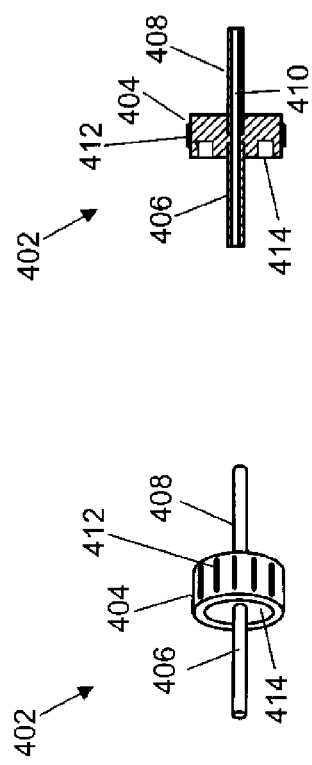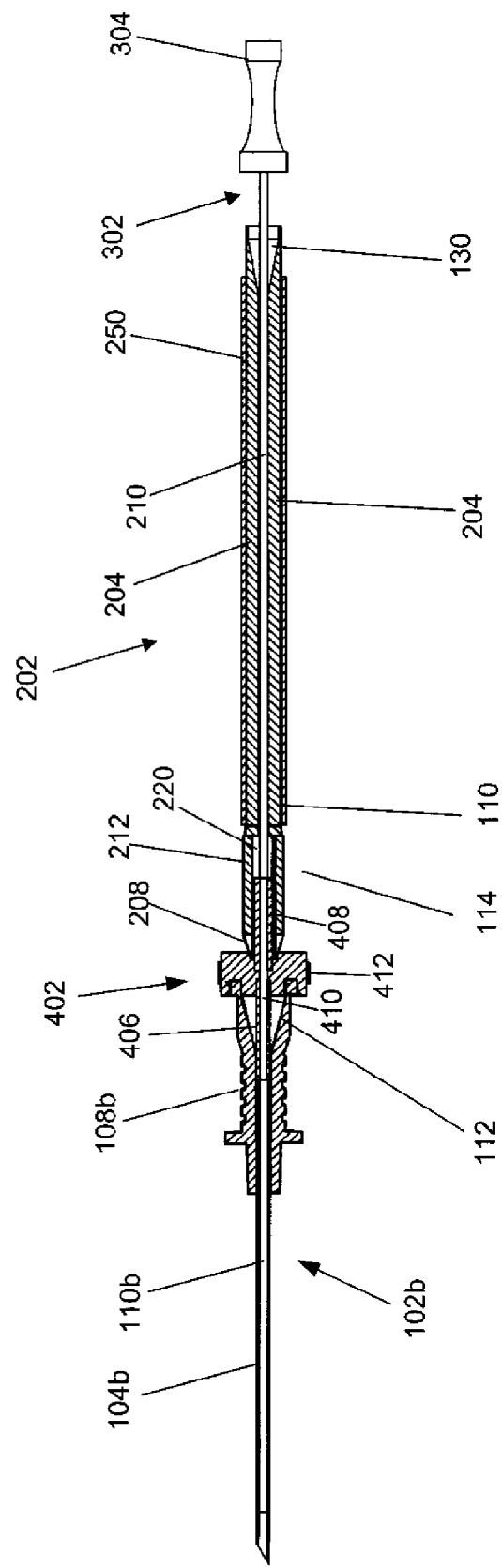

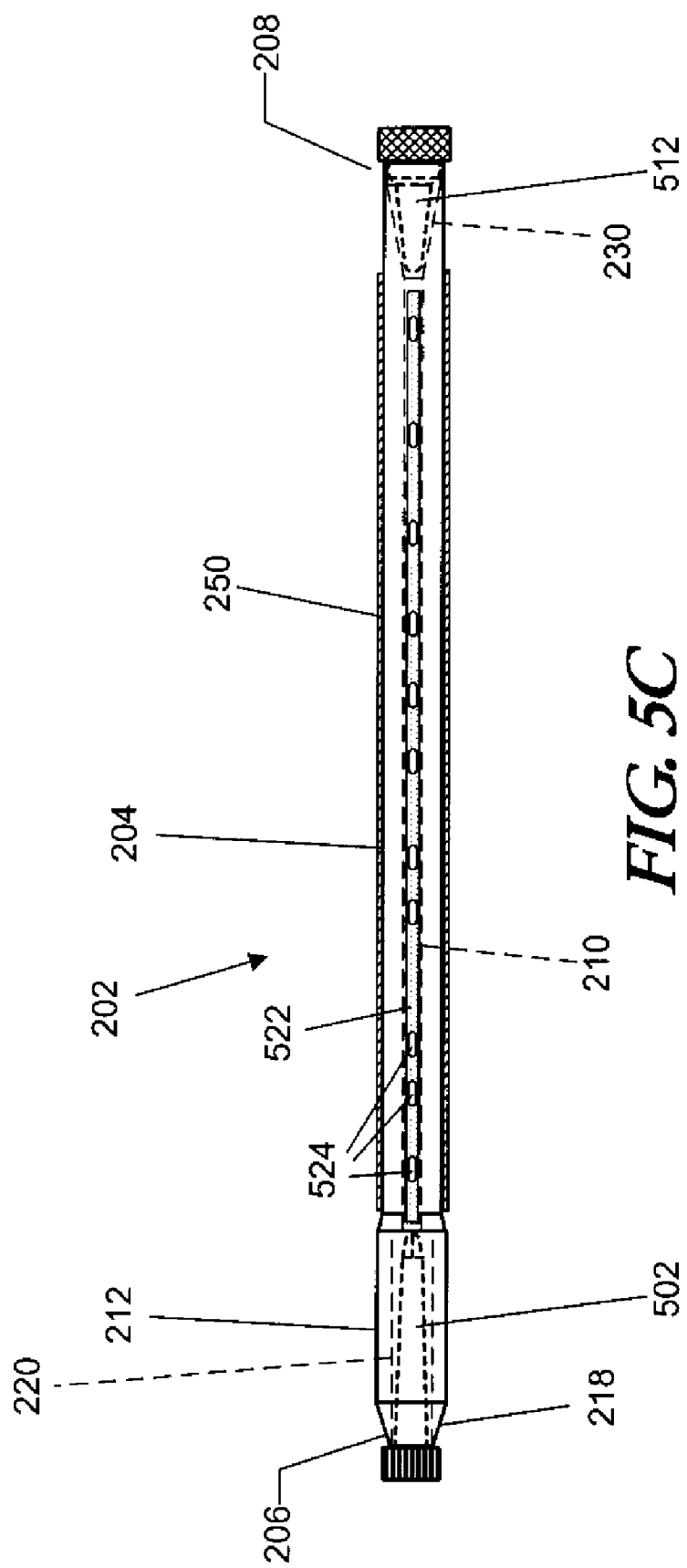

AFTER-LOADER DEVICES AND KITS

This application is a continuation-in-part (CIP) of and claims priority to U.S. patent application Ser. No. 11/592,909, filed Nov. 3, 2006, which is entitled AFTER-LOADER FOR POSITIONING IMPLANTS FOR NEEDLE DELIVERY IN BRACHYTHERAPY AND OTHER RADIATION THERAPY, and which is incorporated herein by reference.

This U.S. Patent Application also claims priority under 35 U.S.C. 119(e) to U.S. Provisional Patent Application No. 60/799,161, which was filed May 9, 2006, and U.S. Provisional Patent Application No. 60/847,834, which was filed Sep. 28, 2006, each of which is entitled AFTER-LOADER FOR POSITIONING IMPLANTS FOR NEEDLE DELIVERY IN BRACHYTHERAPY AND OTHER RADIATION THERAPY, and each of which is incorporated herein by reference.

CROSS REFERENCE TO RELATED APPLICATION

This application relates to U.S. patent application Ser. No. 11/741,658, filed Apr. 27, 2007, which is entitled METHODS FOR USING AFTER-LOADERS.

FIELD OF THE INVENTION

This invention relates to devices and methods that are used for transferring implants to needles used in brachytherapy.

BACKGROUND

Brachytherapy is a general term covering medical treatment which involves placement of radioactive sources near a diseased tissue and can involve the temporary or permanent implantation or insertion of radioactive sources into the body of a patient. The radioactive sources are located in proximity to the area of the body which is being treated. A high dose of radiation can thereby be delivered to the treatment site with relatively low doses of radiation to surrounding or intervening healthy tissue. Exemplary radioactive sources include radioactive seeds, radioactive rods and radioactive coils.

Brachytherapy has been used or proposed for use in the treatment of a variety of conditions, including arthritis and cancer. Exemplary cancers that can be treated using brachytherapy include breast, brain, liver and ovarian cancer and especially prostate cancer in men. For a specific example, treatment for prostate cancer can involve the temporary implantation of radioactive sources (e.g., rods) for a calculated period, followed by the subsequent removal of the radioactive sources. Alternatively, radioactive sources (e.g., seeds) can be permanently implanted in the patient and left to decay to an inert state over a predictable time. The use of temporary or permanent implantation depends on the isotope selected and the duration and intensity of treatment required.

Permanent implants for prostate treatment include radioisotopes with relatively short half lives and lower energies relative to temporary seeds. Exemplary permanently implantable sources include iodine-125, palladium-103 or cesium-131 as the radioisotope. The radioisotope can be encapsulated in a biocompatible casing (e.g., a titanium casing) to form a "seed" which is then implanted. Temporary implants for the treatment of prostate cancer may involve iridium-192 as the radioisotope. For temporary implants, radioactive rods are often used.

Conventional radioactive seeds are typically smooth sealed containers or capsules of a biocompatible material, e.g., titanium or stainless steel, containing a radioisotope within the sealed chamber that permits radiation to exit through the container/chamber walls. Other types of implantable radioactive sources for use in radiotherapy are radioactive rods and radioactive coils, as mentioned above.

Preferably, the implantation of radioactive sources for brachytherapy is carried out using minimally-invasive techniques such as, e.g., techniques involving hollow needles. It is possible to calculate a desired location for each radioactive source which will give the desired radiation dose profile. This can be done using knowledge of the radioisotope content of each source, the dimensions of the source, accurate knowledge of the dimensions of the tissue or tissues in relation to which the source is to be placed, plus knowledge of the position of the tissue relative to a reference point. The dimensions of tissues and organs within the body for use in such dosage calculations can be obtained prior to or during placement of the radioactive sources by using conventional diagnostic imaging techniques including X-ray imaging, magnetic resonance imaging (MRI), computed tomography (CT) imaging, fluoroscopy and ultrasound imaging.

During the placement of the radioactive sources into position, a surgeon can monitor the position of tissues such as the prostate gland using, e.g., ultrasound imaging or fluoroscopy techniques which offer the advantage of low risk and convenience to both patient and surgeon. The surgeon can also monitor the position of the relatively large needle used in implantation procedures using ultrasound or other imaging.

As mentioned above, brachytherapy typically employs hollow needles that are insertable into a patient's body, often with the assistance of a template. A typical template used to guide and/or inform the positioning of hollow needles at a surgical site can provide access to more than one hundred locations. The number of locations can be so numerous that a typical pitch between needle access points can include a pitch of 5 mm.

A hollow needle, as explained above, is used to implant radioactive sources and/or other types of treatment elements into patient tissue at a desired location and to a desired depth. Such treatment elements, which are implantable using the hollow needle, shall be collectively referred to as an implant. Such an implant can be an elongate treatment member, such as a strand that includes a plurality of radioactive sources (e.g., seeds) spaced apart from one another within a bioabsorbable material. Besides a strand, an implant can be another type of treatment member that includes a plurality of radioactive sources spaced apart from one another, such as a member formed of seeds and spacers that are frictionally or otherwise connected to one another (e.g., as described in U.S. Pat. Nos. 6,010,446 and 6,450,939, which are incorporated herein by reference). An elongate treatment member may also be made from a hollow tube that includes a plurality of seeds and spacers loaded within a bore of the tube, with the tube possibly heat shrunk around the seeds and spacers, or the ends of the tube otherwise closed. Alternatively, an implant can be a plurality of loose seeds and loose spacers axially aligned one behind the other. It is also possible that the implant be a single loose radioactive source. Other possibilities also exist, as would be appreciated by one of ordinary skill in the art. For example, an implant can include one or more radioactive rod or coil. An implant can also include one or more seed that has anchoring mechanisms, exemplary details of which are provided in commonly assigned U.S. patent application Ser. No. 11/187,411, entitled "Implants for Use in Brachytherapy and Other Radiation Therapy That Resist Migration and Rotation," filed Jul. 22, 2005. Alternatively, the implant can be or include some other object and need not be radioactive, e.g. a spacer, a marker, or a thermal seed that gives off heat.

Various types of hollow needles can be used in brachytherapy, examples of which are shown in FIGS. 1A and 1B. A first type of needle, shown in FIG. 1A, is often referred to as an applicator needle, and is sometimes marketed under the trademark MICK® needle. Referring to FIG. 1A, an applicator needle 102a is shown as including a hollow needle 104a (also referred to as a cannula) with a blunt or un-sharpened distal end 106a, and a hub 108a positioned at a proximal end. The hub 108a, as shown, has a generally simple cylindrical shape. An exemplary length of the entire needle 102a including the hub is about 7⅞ inches (about 20 cm), with the hub 108a having a length of about 1 inch (about 2.5 cm). As shown in FIG. 1A, the hub 108a surrounds a proximal portion of the cannula 104a. A bore 110a (also referred to as a lumen) extends through the applicator needle 102a. An exemplary diameter of the bore 110a (i.e., the inner diameter of the canuula 104a) is about 0.042 inches.

When an applicator needle 102a is used in brachytherapy, a sharp stylet (not shown) is inserted through the lumen 110a of the hollow needle, so that the sharp distal end of the sharp stylet (e.g., a trocar tip) extends past the blunt distal end 106a of the applicator needle 102a. The needle 102a, with the sharp stylet point extending out its blunt distal end 106a, can then be inserted into patient tissue at a desired location, including to a desired depth. Thereafter, the sharp stylet is removed, and an implant (e.g., a strand, seeds and spacers, or combinations thereof) is loaded into the needle through the proximal end of the needle. Tweezers or the like can be used to insert a strand or other treatment member, and/or loose seeds and spacers, into the proximal end of the needle. However, this can be very difficult and time consuming due to the small inner diameter of the hollow needle. A blunt ended stylet (not shown) can then be inserted into the proximal opening of the needle 102a, until the distal end of the stylet contacts the proximal end of the treatment member (or most proximal seed or spacer). The needle can then be refracted with the stylet held in position so that the implant is deposited at a desired location.

Alternatively, an applicator device, such as a MICK® applicator, can be attached to the proximal end of the applicator needle 102a, and the applicator device can be used to dispose loose seeds (and optionally loose spacers) through the needle 102a and into patient tissue. The MICK® applicator is available from Mick Radio-Nuclear Instruments, Inc., Mount Vernon, N.Y. Details of the MICK® applicator are provided in U.S. Pat. No. 5,860,909.

Referring now to FIG. 1B, a second type of needle 102b, which shall be referred to herein as a locking hub needle for reasons that will be apparent (and sometimes referred to as a prostate seed needle, a standard needle, or a seed lock needle), includes a cannula 104b, a sharpened distal end 106b (e.g., a beveled end), and a hub 108b positioned at a proximal end. The hub 108b has an enlarged diameter with a funneled proximal portion 112, and threads 114 on an outer circumference, that may be used, e.g., to connect the hub 108b to a syringe. The funneled distal end 112 allows a more forgiving tolerance for inserting implants into a lumen 110b of the cannula 104b (if tweezers or the like are used to insert a treatment member and/or loose seeds and spacers into the proximal end of the needle). Nevertheless, even though the proximal funneled opening of needle 102b is larger then the proximal opening of needle 102a, it can still be very difficult and time consuming to load an implant into the needle 102b.

Such needles 102b are typically plugged at the distal end with bonewax or some other plugging material, and pre-loaded with a treatment member and/or loose seeds and spacers, prior to the needle 102b being inserted into patient tissue. Alternatively, such needles 102b can be loaded (i.e., after-loaded) with a treatment member and/or loose seeds and spacers after the needle 102b is inserted into patient tissue.

An exemplary length of the entire needle 102b, including the hub, is about 8⅞ inches (about 22.5 cm). An exemplary length of the hub 108b is about 1 inch (about 2.5 inches). Here, only a portion of the hub 108a surrounds a proximal portion of the cannula 104b, so that the funneled portion 112 can have a larger diameter than the diameter of the cannula 104b. An exemplary diameter of the bore 110b (i.e., the inner diameter of the canuula 104b) is about 0.042 inches.

It has generally been difficult and time consuming for physicians to load a hollow needle (e.g., 102a or 102b) with a treatment member and/or loose seeds and spacers, especially after the needle has been inserted into patient tissue. It would be beneficial if devices and methods were provided for simplifying and expediting such procedures.

SUMMARY OF EMBODIMENTS OF THE INVENTION

Embodiments of the present invention relate to devices, referred to as after-loader devices, that are useful for loading an implant into a hollow needle after the needle is inserted into patient tissue. Embodiments of the present invention also relate to kits that include such after-loader devices, as well as methods for using after-loader devices.

In accordance with specific embodiments, an after-loader device is especially useful for a connecting to a hollow needle, known as an applicator needle, which has a simple cylindrical needle hub at the proximal end of the needle. The after-loader includes an elongated body having a proximal end and a distal end, with a bore extending axially through the body between the proximal and distal ends. A main portion of the bore has a first inner diameter that is approximately equal to the inner diameter of the hollow needle to which the after-loader attaches. A distal portion of the bore has a second inner diameter that is larger than the outer diameter of the needle hub, with the distal portion of the bore being configured to connect to the cylindrical needle hub of the hollow needle. In accordance with an embodiment, a depth of the distal portion of the bore is sufficient to enable the body of the after-loader device to rigidly connect to the cylindrical needle hub of the hollow needle without requiring additional support. A proximal portion of the bore can be funneled to assist with inserting an implant and/or a stylet into the bore.

In accordance with specific embodiments, the after-loader device includes a radiation shield configured to slide over an outer circumferential surface of a main portion of the body, to thereby cover the main portion of the body. The body of the after-loader can be translucent or transparent so that a user can observe an implant loaded into the bore, when the radiation shield is at least partially removed.

In accordance with specific embodiments, a distal portion of the body of the after-loader has an outer diameter that is greater than an outer diameter of the main portion of the body, and greater than an inner diameter of the radiation shield. Such distal portion of the body provides a stop for the radiation shield, and also accommodates the distal portion of the bore. Additionally, a tapered outer circumference, that extends between the distal portion of the body and the main portion of the body, can provide a friction fit between the body and the radiation shield.

In accordance with specific embodiments, the after-loader device includes a distal end plug to plug a distal opening of the bore, and a proximal end plug to plug a proximal opening of the bore. The distal end plug and the proximal end plug, when respectively plugged into the distal and proximal openings of the bore, prevent an implant loaded in the bore from falling out of the bore. Such end plugs can each include a gripping portion and an insertion portion, and can be made from a radiation blocking material.

In accordance with an embodiment, a tapered nose at the distal end of the body is configured to fit into a hub of a second type of hollow needle, such as a locking hub needle.

In further embodiments of the present invention, the after-loader device includes an adapter for use in connecting the body of the after-loader device to a second type of hollow needle, such as a locking hub needle. Such an adaptor can include a central portion, a distal hollow shaft and a proximal hollow shaft. The distal hollow shaft is for insertion into a hub of the second type of needle and into a proximal most portion of a lumen of the second type of needle. The proximal hollow shaft if for insertion into the distal portion of the bore of the body of the after-loader device. The central portion of the adaptor can includes inner threads, for engaging threads on the hub of the second type of needle.

Embodiments of the present invention are also related to brachytherapy kits. Such a kit can include a plurality of after-loader devices, each of which is useful for loading an implant into a hollow needle after the needle is inserted into patient tissue. The kit can also include a plurality of treatment members, each member loaded into a bore of one of the after-loader devices, and maintained in the bore by end-plugs of the after-loader device. Each such member (e.g., a strand) can include a plurality of radioactive sources spaced apart from one another, e.g., in accordance with a treatment plan. Alternatively, or additionally, an implant loaded into a bore can include a plurality of loose seeds separated from one another by spacers. Each the after-loader device of the kit can include a radiation shield that surrounds at least a main portion of the body of the after-loader device. Also, the kit can include at least one stylet having a length that is at least as long as a total length of the after-loader device connected with a hollow needle, as well as at least one hollow needle. In specific embodiments, the plurality of treatment members of the kit fulfill an entire predetermined treatment plan for a patient. The kit can also include a tray holding the plurality of after-loader devices loaded with the plurality of treatment members, as well as a pouch housing the tray (which is holding the plurality of after-loader devices loaded with the plurality of treatment members). Additionally, depending on the type of hollow needle included in the kit, the kit can also include at least one adaptor configured to connect the after-loader devices to hub of a locking hub hollow needle.

Embodiments of the present invention are also directed to methods for implanting implants into patient tissue. In accordance with an embodiment, a distal end of a hollow needle is inserted into patient tissue at a desired location and to a desired depth. Where the hollow needle does not have a sharpened end, a sharp end of a sharp stylet is extended beyond the distal end of the hollow needle, to assist with the insertion of the needle. Where the needle has a sharpened distal end, such a sharpened stylet need not be used.

Where the needle hub is a simple cylindrical needle hub of a hollow needle known as an applicator needle, the after-loader device can be connected to the cylindrical needle hub by inserting at least a portion of the cylindrical needle hub into a distal portion of a bore of the after-loader, such that the after-loader is rigidly connected to the cylindrical needle hub of the hollow needle without requiring additional support. A stylet is inserted into an opening at a proximal end of the after-loader device, to urge an implant from the after-loader device into a lumen of the hollow needle.

Certain embodiments employ the use of a stylet having a length that is at least as long as a total length of the after-loader device connected with a hollow needle. Where such a stylet is available, the implant can be urged from the after-loader device, through a lumen of the hollow needle, to a distal end of the hollow needle, while the after-loader device is still connected to the needle. Thereafter, the hollow needle and the after-loader device are retracted, while the stylet is held in place, to thereby deposit the implant at the desired location and to the depth.

In specific embodiments, the implant can be loaded into the bore of the after-loader device, after the after-loader device is connected to the hollow needle, but before the stylet is inserted into the after-loader device. In other embodiments, the implant was already loaded into the bore of the after-loader device before the after-loader device is connected to the hollow needle.

In specific embodiments, where the after-loader device includes end plugs, the end plugs of the after-loader device, which maintain the implant within a bore of the after-loader device, are removed prior to connecting the after-loader device to the hollow needle.

In specific embodiments the implant is a treatment strand or other treatment member, which includes a plurality of radioactive sources spaced apart from one another. Alternatively, or additionally, the implant can be a plurality of loose seeds and spacers. Other implants are also possible, as described below.

Where the stylet to be employed is not as long as a total length of the after-loader device connected with a hollow needle, the stylet is used to urging an implant from the after-loader device, into a lumen of the hollow needle. The stylet is then retracted from the after-loader, and the after-loader is removed, i.e., disconnected from the hollow needle. Thereafter, a stylet (the same or a different stylet) is inserted into an opening at a distal end of the hollow needle, and the stylet is used to urge the implant to a distal end of the hollow needle. Then, the hollow needle is retracted while the stylet is held in place, to thereby deposit the implant at the desired location and to the depth.

Methods of the present invention also include methods that used the adaptor mentioned above. For example, after a distal end of a hollow needle is inserted into patient tissue, a distal hollow shaft of an adaptor can be inserted through the needle hub and into a proximal portion of a lumen of the hollow needle, and an after-loader device can be connected to a proximal hollow shaft of the adaptor. It is also possible that the adaptor, just described, already be connected to the proximal portion of a hollow needle, when the distal end of the hollow needle is inserted into patient tissue. A stylet can then be inserted into an opening at a proximal end of the after-loader device. Depending upon the length of the stylet, the after-loader body and adaptor may be left in place during the remainder of the implant procedure, or may need to be removed before a stylet is used to urge the implant to the distal end of the hollow needle. The hollow needle (and the after-loader device and adaptor, if still in place) are then refracted, while the stylet is held in place, to thereby deposit the implant at the desired location and to the depth.

This summary is not intended to be a complete description of the invention. Other features, aspects, objects and advantages of the invention can be obtained from a review of the specification, the figures, and the claims.

BRIEF DESCRIPTION OF THE DRAWINGS

FIG. 1A is a side view of first type of hollow brachytherapy needle, often referred to as an applicator needle.

FIG. 1B is a side view of a second type of hollow brachytherapy needle, sometime referred to as a seed lock needle, or a locking hub needle.

FIG. 2A is a side view of an after-loader in accordance with an embodiment of the present invention, with its shield removed.

FIG. 2B is a side view of the after-loader device of FIG. 2A, with its shield in place.

FIG. 2C is a perspective view of the after-loader device of FIGS. 2A & 2B, with its shield removed.

FIG. 2D is a perspective view of the shield of the after-loader device.

FIG. 4A is a perspective view of an adaptor, according to an embodiment of the present invention, which can be used to help connect the after-loader device of FIGS. 2A & 2B to the hollow needle of FIG. 1B.

FIG. 4B is a cross-sectional view of the adaptor of FIG. 4A.

FIG. 4C is a cross-sectional side view of the after-loader device of FIG. 2A mated with the hollow needle of FIG. 1B, using the adapter of FIGS. 4A and 4B, and having a stylet disposed within the bore of the after-loader and adaptor and the hollow needle.

FIG. 5C is a side view of the after-loader of FIGS. 2A-2C (without its shield) with the distal and proximal end plugs of FIGS. 5A and 5B in place.

DETAILED DESCRIPTION

As explained above, it has generally been difficult and time consuming for physicians to load a hollow needle (e.g., 102a or 102b) with a strand and/or loose seeds and spacers, especially after the needle has been inserted into patient tissue. As will be described below, embodiments of the present invention related to devices and methods for simplifying and expediting such procedures. More specifically, embodiments of the present invention relate to devices, referred to as after-loader devices, that are useful for loading an implant into a hollow needle after the needle is inserted into patient tissue. Embodiments of the present invention also relate to kits that include such after-loader devices, as well as methods for using after-loader devices.

As will be described below, an after-loader of the present invention can simplify and/or expedite the loading of an implant into a hollow needle, especially after the needle has been inserted into patient tissue. It is because such a device is useful in loading a hollow needle "after" the needle is inserted into patient tissue, that the device is referred to herein as an "after-loader". Nevertheless, the after-loader device can also be used to pre-load a needle (i.e., load an implant into a hollow needle before the needle is inserted into patient tissue), if desired.

Figure 3A:
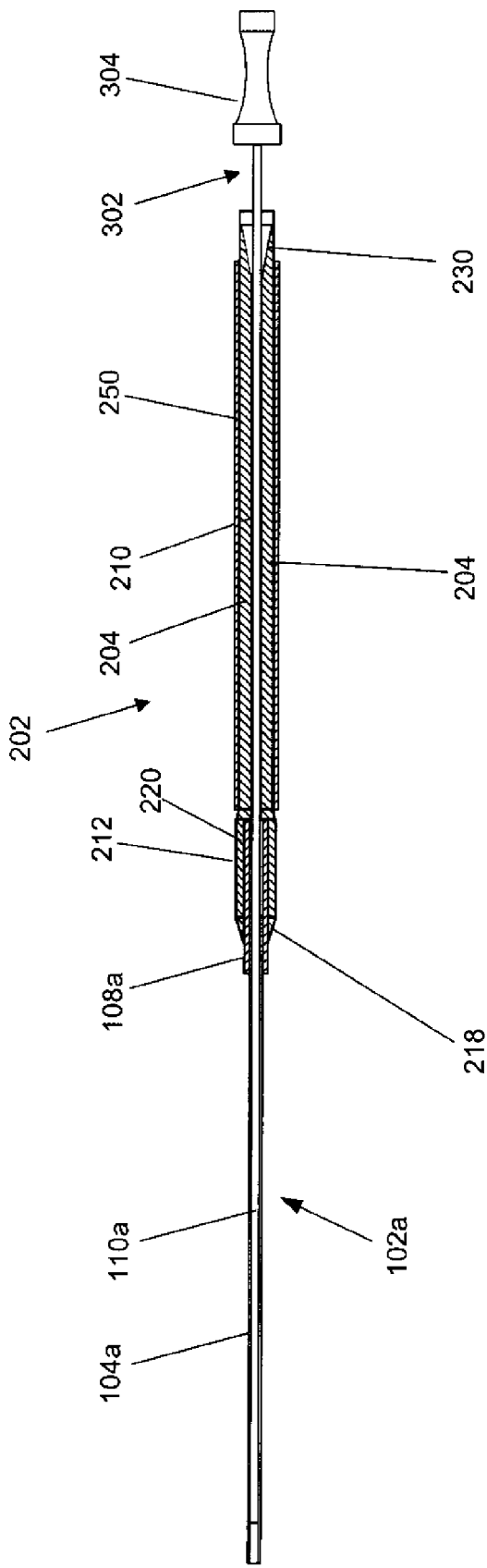
FIG. 3A is a cross-sectional side view of the after-loader of FIG. 2A mated with the needle of FIG. 1A, and having a stylet disposed within the after-loader device and hollow needle.
Figure 3B:
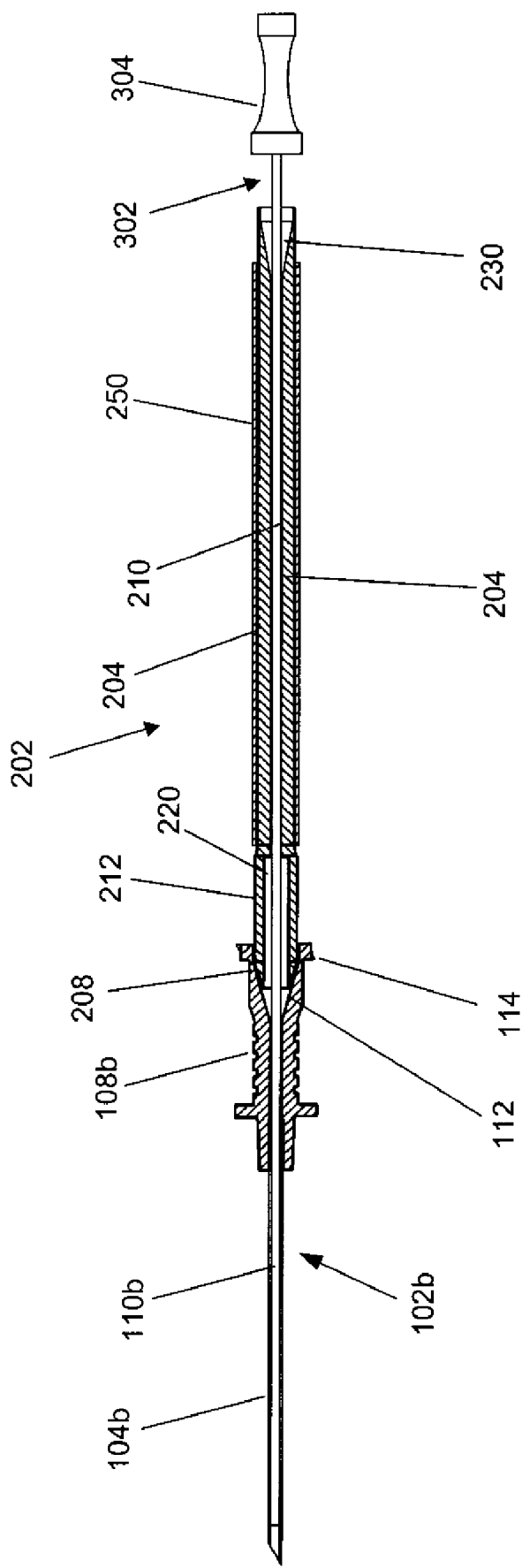
FIG. 3B is a cross-sectional side view of the after-loader of FIG. 2A mated with the hollow needle of FIG. 1B, and having a stylet disposed within the after-loader device and hollow needle.

Referring to FIG. 2A, an after-loader device 202, according to an embodiment of the present invention, is shown. FIG. 2C shows a perspective view of the after-loader device 202, which is also referred to simply as an after-loader 202. The after-loader 202 can be used with the applicator needle 102a of FIG. 1A (as shown in FIG. 3A), or alternatively with the locking hub needle 102b of FIG. 1B (as shown in FIGS. 3B and 4C), providing flexibility in needle choice. The after-loader 202 includes an elongated body 204 having a distal end 206, a proximal end 208, with a bore 210 extending therebetween. The body 204 of the after-loader 202 is shown as having a generally cylindrical shape, however variations on this are possible.

The body 204 of the after-loader 202, or the after-loader 202 in general, includes a distal portion 212, a main portion 214 and a proximal portion 216. In accordance with an embodiment, the main portion 214 of the after-loader 202 includes a generally constant outer diameter (e.g., 0.162 inches), and a generally constant inner diameter (e.g., 0.055 inches), with the inner diameter being about the same as the inner diameter of the needle with which the after-loader 202 will interface (as mentioned above, the inner diameter of the cannula of the hollow needles 102a and 102b can be about 0.042 inches). More generally, the diameter of the bore 210 that extends through the main portion 214 of the after-loader 202 should be slightly larger than the outer diameter of the implant (e.g., strand, seed(s) and/or spacer(s)) that is to be loaded into the after-loader 202. In certain embodiments, the inner diameter of the bore 210 of the main portion 214 of the after-loader 202 can have one or more step, and/or have a taper (rather than having a constant inner diameter), such that the proximal end of the bore 210 within the main portion 214 has a slightly larger diameter than the distal end of the bore 210 within the main portion 214.

In the embodiment shown, the distal portion 212 of the after-loader 202 includes an enlarged outer diameter (e.g., 0.188 inches), which tapers at each end. More specifically, at the proximal end of the distal portion, the distal portion 212 tapers at a small angle θ (e.g., 5 degrees) until the diameter of the main portion 214 of the body 204 (e.g., 0.162 inches) is reached. The purpose of this taper 219 is to provide a friction fit for a shield 250 that slides over the rest of the after-loader 202, the friction fit being attributable to the increase in diameter toward the distal portion 210. The shield 250 is positioned around the after-loader 202 to reduce or minify an amount of radiation that escapes from the after-loader 202 where implants placed in the after-loader 202 are radioactive. FIG. 2B shows the after-loader 202 with its shield 250 in place. FIG. 2D shows a perspective view of the shield 250.

Referring to FIGS. 2A and 2C, the taper at the distal end of the distal portion 212 forms a nose 218 of the after-loader 202, which is tapered at an angle α generally corresponding to an angle of the funneled proximal portion 112 of the locking hub needle 102b. Thus, an external angle of the nose 218 can be approximately 15 degrees in angle, in an embodiment wherein a typical locking hub needle 102b is to be accommodated. The nose 218 of the after-loader 202 can be positioned within the funneled portion 112 of the locking hub needle 102b, so that the after-loader 202 is removably mated with the hub 108b of the locking hub needle 102b, as can be appreciated from FIG. 3B, discussed in more detail below. It is also possible that an after-loader 202 not include a tapered nose 218.

A funneled portion 230 of the bore 210 of the after-loader 202 can be funneled at an angle β to simplify insertion of an implant and stylet into the bore 210 of the after-loader 202. For example, the funnel can cause an increase in diameter at a 5 to 10 degree angle, and specifically at an 8 degree angle. Such funneled portion 230 of the bore 210 extends through the proximal portion 216 of the body 204.

In accordance with an embodiment, the body 204 of the after-loader 202 can be made of a transparent or translucent material, such as a medial grade plastic, e.g., acrylic, polycarbonate or other plastic, that enables a user (e.g., physician, clinician, physicist, etc.) to visually verify the contents (i.e., implant) loaded in the after-loader 202. Where the after-loader 202 is made of a plastic, the after-loader 202 may not sufficiently restrict radiation from escaping the after-loader 202. Accordingly, the shield 250 is employed to reduce and preferably prevent leakage. As shown in FIG. 2D, the shield 250 can be a hollow cylinder formed of a material (e.g., stainless steel) that sufficiently restricts the amount of radiation that escapes the shield 250. In such embodiments, the shield 250 can be slid back (i.e., toward the proximal end of the after-loader 202) to reveal the contents of the after-loader 202, for visual verification purposes. In other embodiments, the after-loader 202 itself can be made from a material more opaque to radiation, such as stainless steel, or a plastic impregnated with lead, or some other shielded plastic.

Referring to FIGS. 2A-2C, the enlarged outer diameter of the distal portion 212 of the after-loader 202 serves two purposes. First, it enables the diameter of a distal portion 220 of the bore 210 to be enlarged to accommodate the hub 108a of the applicator needle 102a, as discussed in more detail below. Further, it acts as a stop to hold the shield 250 in place at the proper location after the shield 250 has been slid over the proximal end 208 of the after-loader 202.

In accordance with an embodiment, the inner diameter of the distal portion 212 of the after-loader 202 is larger than the inner diameter of the main portion 214 of the after-loader 202, so that the hub 108a of the applicator needle 102a can be accepted therein. In other words, the diameter of the distal portion 220 of the bore 210 (which is the portion of the bore 210 within distal portion 212) is larger than the diameter of the main portion of the bore 210 (i.e., the portion of the bore 210 extending through the main portion 214 of the body 204). More specifically, the distal opening of the portion 220 of the bore 210, extending from the distal end 206 towards the proximal end 208 of the body 204, has a diameter that is slightly larger than the outer diameter of the hub 108a of the applicator needle 102a, so that the distal portion 220 of bore 210 is configured to receive, and thereby connect to, the hub 108a of the applicator needle 102a. For example, the diameter of the distal portion 220 of the bore 210 can be 0.099 inches, while the diameter of the main portion of the bore 210, which roughly corresponds to the inner diameter of a hollow needle, can be from anywhere from about 0.042 to 0.055 inches. In specific embodiments, the distal portion 220 of the bore 210 has a slight taper from its opening rearward (e.g., an opening diameter of 0.105 inches tapers to 0.985 inches), so that a slight friction fit can be provided between the distal portion 220 of the bore 210 and the hub 108a accepted therein (presuming the outer diameter of the hub 108a is less than 0.105 inches, but greater than 0.985 inches).

Additionally, a depth d of the distal portion 220 of the bore 210 is preferably sufficient to enable the body 204 of the after-loader 202 to rigidly connect to the hub 108a of the needle 102a without requiring any additional support, e.g., from a user or some support structure (e.g., a support rod). Preferably such depth d is at least ¼ inch, and more preferably about ½ inch. However, other depths will work, and are within the scope of the present invention.

FIG. 3A shows a cross-section of the after-loader 202 accepting the hub 108a of an applicator needle 102a. FIG. 3A also shows a stylet 302, including a handle 304 at its proximal end, inserted through the bore 210 of the after-loader 202 and the lumen 110a of the applicator needle 102a. As mentioned above, the diameter of the distal portion 220 of the bore 210 of the after-loader is slightly larger than the outer diameter of the hub 108a, so the hub 108a fits therein.

FIG. 3B shows a cross-section of the after-loader 202 with its nose 218 within the funneled portion 112 of a locking hub needle 102b. FIG. 3A also shows a stylet 302, including a handle 304 at its proximal end, inserted through the bore 210 of the after-loader 202 and the lumen 110b of the locking hub needle 102b. When used in the manner shown in FIG. 3B, the after-loader 202 may need to be supported by the user, to prevent the after-loader from disengaging from the hub 108b of the needle 102b. To ensure that no such user support is needed, an adaptor 402 of an embodiment of the present invention can be used, as will now be explained with reference to FIGS. 4A-4C.

FIG. 4A is a perspective view of the adaptor 402, in accordance with an embodiment of the present invention. FIG. 4B is a cross-section of the adaptor 402. The adaptor 402 includes a central portion 404, from which extends a distal hollow shaft 406 and a proximal hollow shaft 408. The hollow shafts 406 and 408 can be discontinuous (i.e., separate from one another), as shown in FIG. 4B. Alternatively, the distal and proximal shafts 406 and 408 can be parts of a continuous shaft that extends through the central portion 404. A bore 410 extends axially through the entire adaptor 402, whether or not the shafts 406 and 408 are continuous. The diameter of the bore 410 should be sufficient to allow an implant to pass there-through. Thus, the diameter of the bore 410 can be similar to the diameter of the bores 110a and 110b of needles 102a and 102b, which can be similar to the diameter of the major portion of the bore 210 of the after-loader 202 as discussed above.

Referring to FIG. 4C, the distal hollow shaft 406 of the adaptor 402 is intended to fit within the proximal end of hub 108b of locking hub needle 102b, and into a most proximal portion of the lumen 110b of the cannula 104b. Additionally, the central portion 404 can include inner threads 414 to engage the outer threads 114 of the hub 108b of the locking hub needle 102b. An outer circumference 412 of the central portion 404 can be textured, to make it easier for a user to turn the adaptor 402 so it screws onto threads 114 of the hub 108b. The proximal hollow shaft 408 is intended to fit in the enlarged distal portion 220 of the bore 210 of the after-loader 202.

One or more empty after-loader 202 can be provided to a user, so that the user can load each after-loader 202 with an implant and thereafter use the after-loader(s) 202 during an brachytherapy procedure. In another embodiment, one or more already loaded after-loader 202 (i.e., a pre-loaded after-loader) can be provided to a user. More specifically, a facility can load implants into a plurality of after-loaders 202, and provide such pre-loaded after-loaders to a user. The pre-loaded after-loaders 202 can include all the implants that are necessary to fulfill a predetermined patient specific treatment plan. In specific embodiments, each after-loader is pre-loaded with a corresponding strand or other treatment member that has been manufactured to meet a treatment plan. Such pre-loaded after-loaders 202 can be delivered in a tray having a unique number for each of the pre-loaded after-loaders 202, so that the user knows which strand or other member is located in which after-loader, and thus knows, where each strand or other member should be implanted. It is also possible that such numbers or similar designations are printed directly on the after-loaders 202. When pre-loaded after-loaders 202 are provided to a user, it is preferred that each pre-loaded after-loader 202 is covered by its shield 250. Also, the packaging that is used to store the plurality of pre-loaded after-loaders can include further shielding, e.g., a lead plate can cover a row of pre-loaded after-loaders that are within a tray.

Figure 5A:
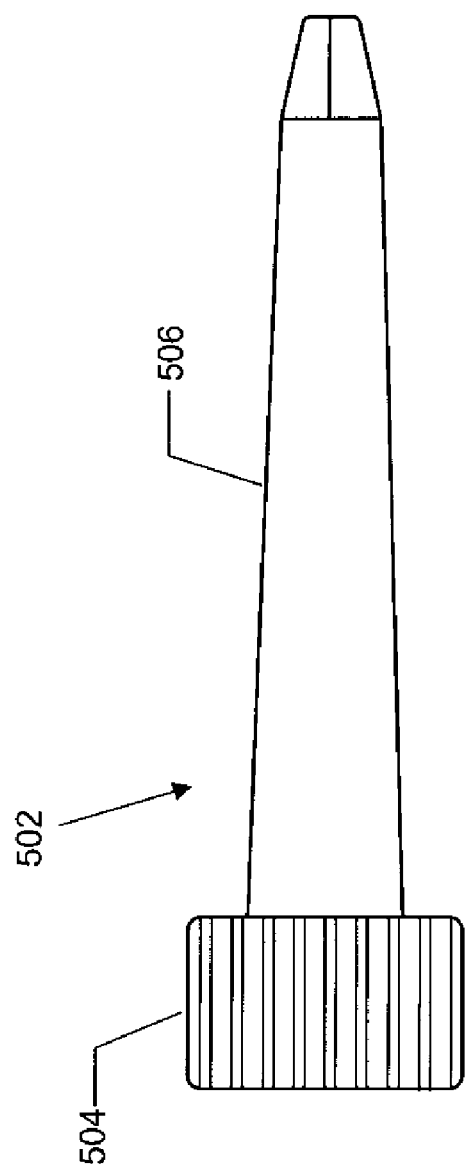
FIG. 5A is a side view of a distal end plug for an after-loader, in accordance with an embodiment of the present invention.
Figure 5B:
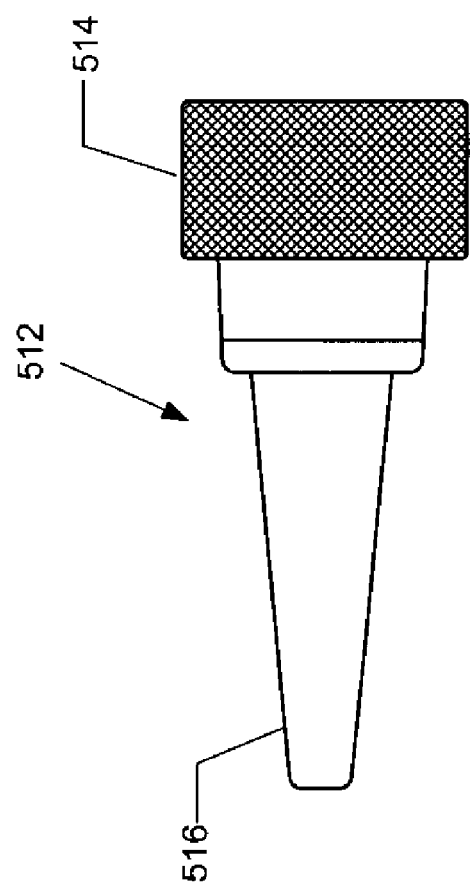
FIG. 5B is a side view of a proximal end plug for an after-loader, in accordance with an embodiment of the present invention.

When the after-loader 202 is shipped pre-loaded with a treatment member (e.g., strand), or other implant, the openings at the proximal and distal ends 206 and of the after-loader 202 are preferably plugged, to prevent the treatment member or other implant from unintentionally falling out of the after-loader 202. Referring to FIG. 5A, a distal end plug 502, according to an embodiment of the present invention, is shown. FIG. 5B shows a proximal end plug 512, according to an embodiment of the present invention.

FIG. 5C shows a side view of a pre-loaded after-loader 202, which is pre-loaded with a strand 502. The strand 522 includes a plurality of radioactive seeds 524 that are spaced apart from one another, e.g., in accordance with a treatment plan. A cut-away view of the shield 250 is provided, so that it can be seen that the strand 522 is within the bore 210 of the after-loader 202. The opening at the distal end 206 of the after-loader 202 is plugged with the distal end plug 502. Similarly, the opening at the proximal end 208 of the after-loader 202 is plugged with the proximal end plug 512. In addition to preventing a treatment member (e.g., strand) or other implant from falling out of the after-loader 202, the end plugs 502 and 512 can also be employed to block radiation from emitting from the ends of the after-loader 202. If that is desired, the end plugs 502 and 512 should be made of a material that blocks radiation, e.g., stainless steel. Alternatively, the end plugs 502 and 512 need not block radiation, and can be made of plastic or the like.

The distal end plug 502 includes a grip portion 504, that can be gripped to insert the insertion portion 506 of the distal end plug 502 into the opening at the distal end 206 of the after-loader 202. The diameter of the grip portion 504 is greater than the diameter of the distal portion 220 of the bore 210. The diameter of the insertion portion 506 of the distal end plug 502 is sized so that it fits within the distal portion 220 of the bore 210, yet creates a friction fit so the end plug 502 does not inadvertently fall out. In accordance with an embodiment, a length or depth of the insertion portion 506 of the distal end plug 502 is about the same as the depth of the distal portion 220 of the bore 210. This will keep the distal end of the treatment member (e.g., strand) or other implant within the confines of the shield 250.

Similarly, the proximal end plug 512 includes a grip portion 514, that can be gripped to insert the insertion portion 516 of the proximal end plug 512 into the opening at the proximal end 208 of the after-loader 202. The diameter of the grip portion 514 is greater than the largest diameter of the funneled portion 230 of the bore 210. The diameter of the insertion portion 516 of the proximal end plug 512 is sized so that it fits within the funneled portion 230 of the bore 210, yet creates a friction fit so the end plug 512 does not inadvertently fall out. In accordance with an embodiment, a length or depth of the insertion portion 516 of the proximal end plug 512 is about the same as the depth from the proximal end 208 to the most distal point of the funnel 230. This will keep the proximal end of the treatment member (e.g., strand) or other implant within the confines of the shield 250.

Figure 6B:
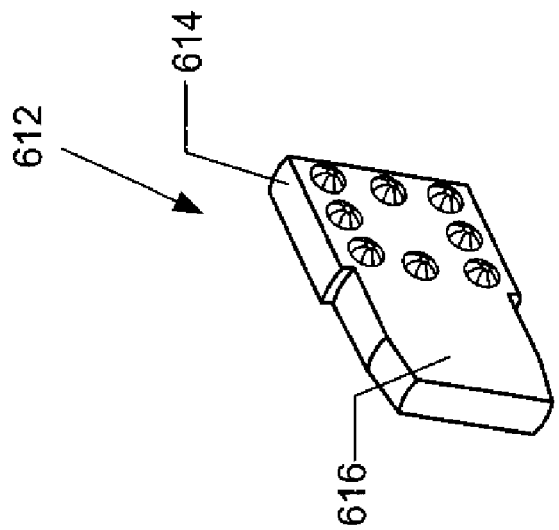
FIG. 6B is a side view of a proximal end plug for an after-loader, in accordance with another embodiment of the present invention.
Figure 6A:
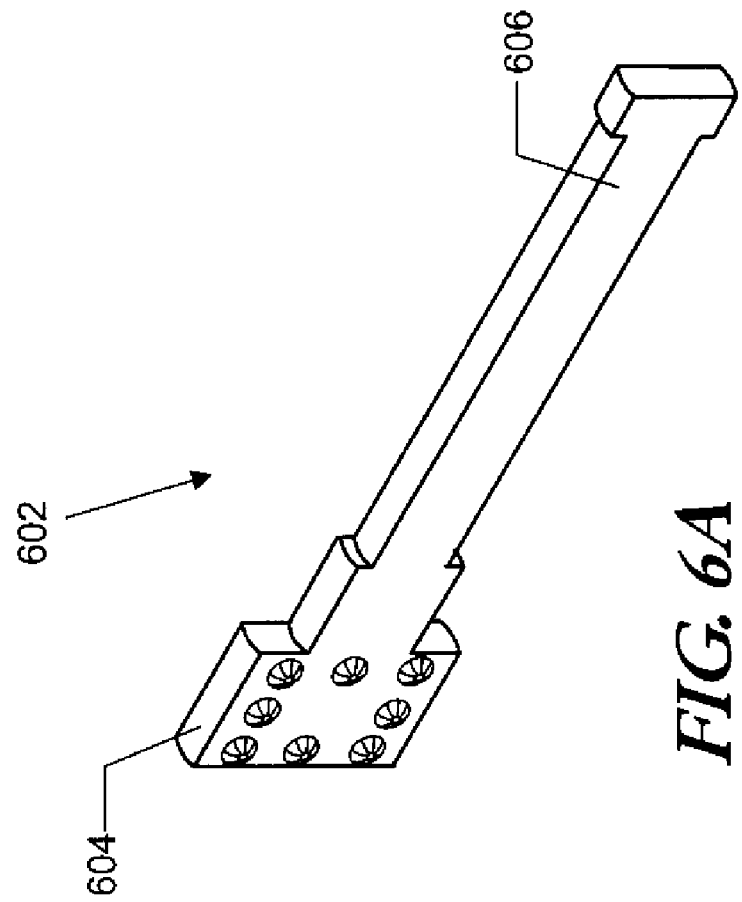
FIG. 6A is a side view of a distal end plug for an after-loader, in accordance with another embodiment of the present invention.

It should be noted that the end plugs 502 and 512 need not be shaped as shown in FIGS. 5A and 5B. The end plugs need only be shaped so as to function to maintain the implant within the after-loader 202. For example, where radiation emission from the implant is not a concern, the end plug need not function to block radiation. Alternative designs for the end plugs are shown in FIGS. 6A and 6B, which, respectively, show an alternative distal and plug 602 and alternative proximal end plug 612. Instead of using end plugs, or in addition to using end plugs, an elongate treatment member (that is loaded within the bore 210 of the after-loader 202) can include one or more bumps, rings, wings, polymeric hairs or other protrusions that frictionally maintains the member within the bore 210, until the member is urged out using a stylet.

FIGS. 4A, 5B, 6A and 6B illustrate exemplary embodiments of end plugs for use with after-loaders 202. In other embodiments, some other style of end plugs can be employed to retain an implant with an after-loader 202. In still other embodiments, end plugs for use with the after-loader of the present invention can be integrally formed with an implant housed within the after-loader.

Figure 7:
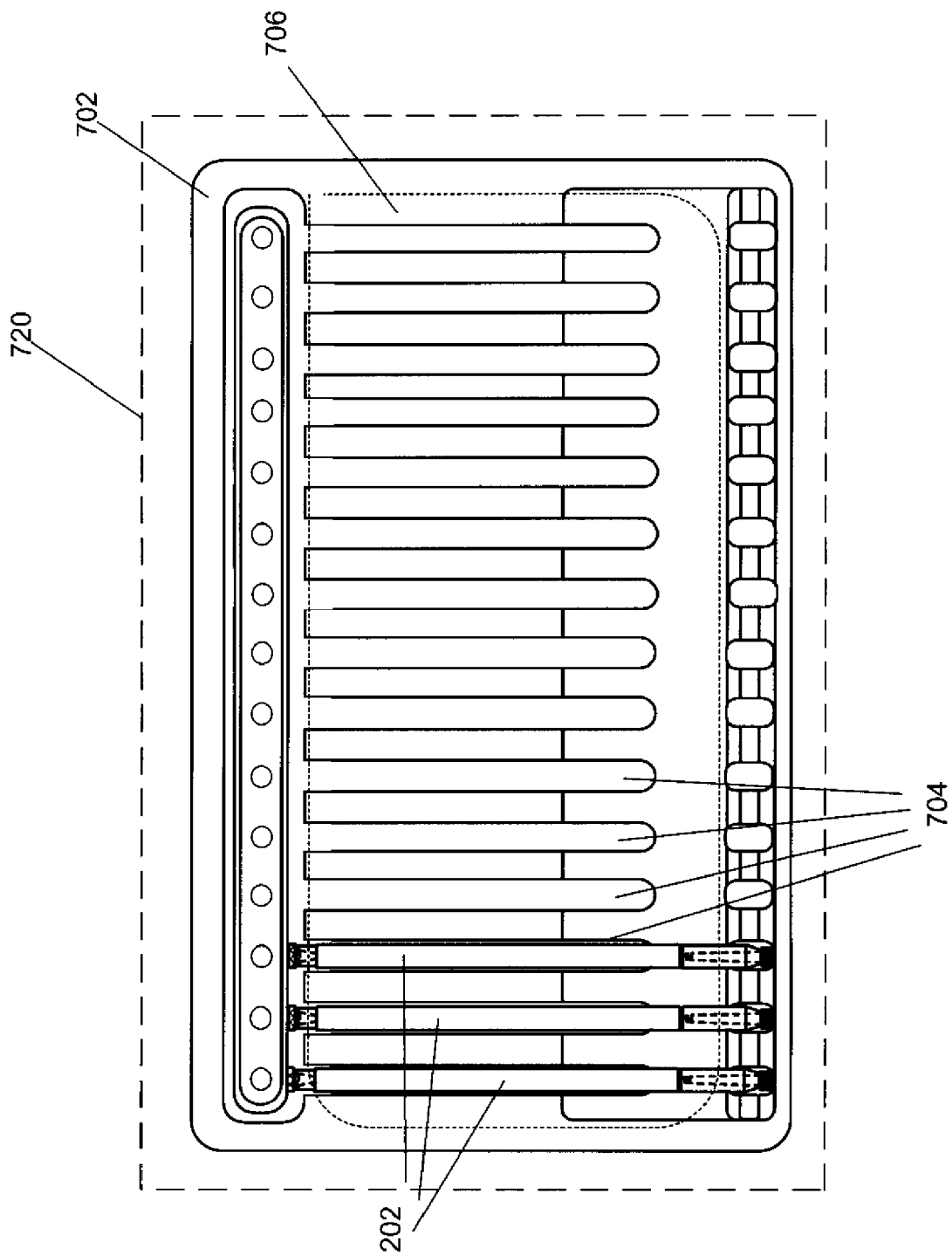
FIG. 7 shows a plurality of after-loaded devices within a tray.

FIG. 7 shows a plurality of pre-loaded after-loaded devices 202 within a tray 702, according to an embodiment of the present invention. The tray 702 is shown as including a plurality of grooves 704, that are configured to frictionally hold fifteen after-loaders 202. Of course, the tray 702 can be configured to hold less or more after-loaders 202. Also shown (in dashed line) is a further radiation shield 706, which provides for some additional radiation shielding. Such a tray 702 can be part of a kit of the present invention, and may also have a cover (not shown), both of which can be placed in a pouch 720. Such a pouch 720, e.g., made of Tyvek™, can keep the contents of the tray 702 sterile until they are ready for use, and the pouch is opened to reveal its contents.

Methods for using the after-loader 202 shall now be described with reference to FIGS. 8 and 9. Steps that are common to each method are numbered in the same manner, to avoid replication of the discussion.

Figure 8:
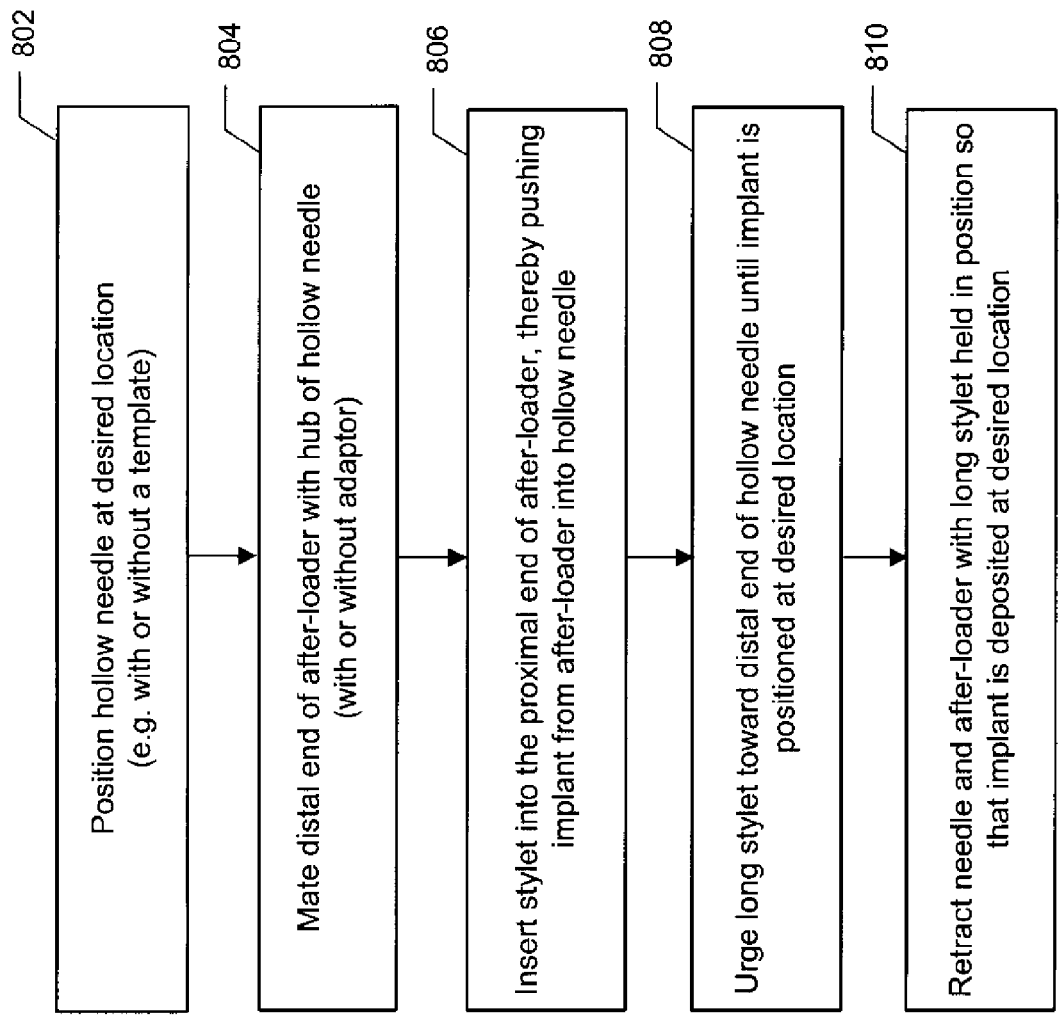
FIG. 8 is a high level flow diagram that is used to summarize a method of using an after-loader, in accordance with an embodiment of the present invention.
Figure 9:
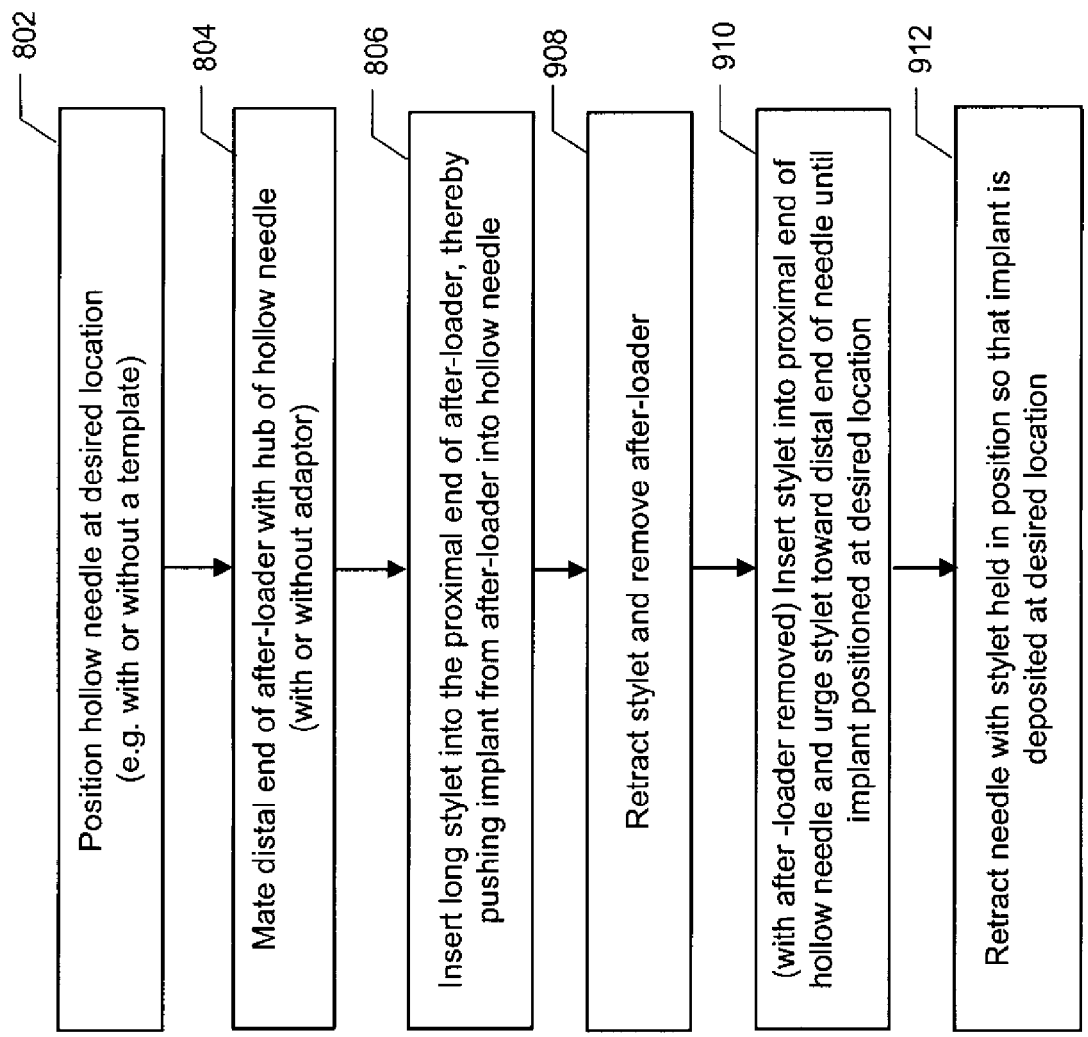
FIG. 9 is a high level flow diagram that is used to summarize a method of using an after-loader, in accordance with an alternative embodiment of the present invention.

Referring to FIG. 8, at step 802, the hollow needle is positioned at the desired location, e.g., with the assistance of a template. At step 804, the hub of the hollow needle is mated with the distal end 206 of the after-loader 202, either by way the enlarged distal portion 220 of the bore 210, the tapered nose 218, or by using the adaptor 402. At step 806, with the implant positioned within the after-loader 202, and the after-loader connected to the hub of the hollow needle, a stylet 302 is inserted into the opening at the proximal end 208 of the after-loader 202. A stylet 302 for use with the after-loader 202 can be sufficient in length to accommodate both the needle 102 and the after-loader 202. Where that is the case, at step 808, the implant is urged toward the distal end of the needle until the implant is positioned at the desired location and depth. Then, the stylet 302 is held in place while the needle and after-loader are retracted, so that the implant is deposited at a desired location, as indicated at step 810. Alternatively, a stylet of less than sufficient length to accommodate both the needle and the after-loader 202 can be employed. When such a stylet is used, the stylet can be used urge the implant from the after-loader 202 to the hollow needle, as indicated at step 806. The stylet can then be removed, and the after-loader 202 disconnected, as indicated at step 908 in FIG. 9. A stylet (the same, or a different stylet) can then be inserted (e.g., reinserted) to urge the implant to the desired location and depth, at step 910. At step 912, the needle can then be retracted with the stylet held in position so that the implant is deposited at the desired location and depth.

As specified above, each after-loader 202 can be employed for use with one or more radioactive or other treatment seed, one or more treatment member (e.g., strand), radioactive rod, radioactive coil, marker, or some other implant. A strand (also referred to as a treatment strand) can include a plurality of radioactive sources spaced apart from one another, e.g. in accordance with a treatment plan. A strand likely includes a bioabsorbable material within which treatment sources (e.g., radioactive seeds) are encapsulated, and spaced apart from one another, e.g., in accordance with a treatment plan.

As specified above, the after-loaders 202 can be pre-loaded with strands, or other implants so that the pre-loaded after-loaders can be provided to a physician. Pre-configured strands or another implant can be loaded into the after-loader 202 off-site and fitted with end plugs at the distal and proximal ends 206 and 208 of the after-loader, and then shipped to the user for a specific patient. Thus, the proper treatment can be determined as part of a pre-plan. In such embodiments, the after-loader preferably would include its shield 250 securely fitted to the outside surface of the after-loader 202. Such pre-loaded after-loaders can simplify and expedite the implantation process. Further, such pre-loaded after-loaders 202 offer benefits to hospitals or clinics that strive to minify the amount of handling of the implants performed by staff.

It is also possible for a physician to load strands into the after-loaders 202. The physician can do this prior to inserting any needles into patient tissue. Alternatively, after needles are inserted into patient tissue, the physician can connect an after-loader 202 to a needle, and then insert the implant into the after-loader 202. Thereafter, the physician would urge the implant from the after-loader 202 into the needle, using a stylet. Other variations are also possible, as would be understood from the description herein.

As will be appreciated, and which can be extrapolated from the embodiments described, the after-loaders 202 can be longer or shorter in length as needed. In accordance with specific embodiments, the after-loader 202 can include an outer diameter that, at a maximum, does not exceed 5 mm in size to generally match the pitch of a typical template. However, in other embodiments, the after-loader 202 can be larger or smaller in diameter.

The previous description of the preferred embodiments is provided to enable any person skilled in the art to make or use the embodiments of the present invention. While the invention has been particularly shown and described with reference to preferred embodiments thereof, it will be understood by those skilled in the art that various changes in form and details may be made therein without departing from the spirit and scope of the invention.

What is claimed is:

1. An after-loader device useful for loading an implant into a hollow needle after the needle is inserted into patient tissue, the hollow needle having a inner diameter, an outer diameter, a distal end, a proximal end, and a cylindrical needle hub at the proximal end, the cylindrical needle hub having an outer diameter that is greater than the outer diameter of the needle, the after-loader device comprising:
an elongated body having a proximal end and a distal end; and
a bore that extends axially through said body between said proximal and distal ends of said body;
wherein a main portion of said bore has a first diameter that is approximately equal to the inner diameter of the hollow needle;
wherein a distal portion of said bore has a second diameter that is larger than the outer diameter of the needle hub and configured to receive, and thereby connect to, the needle hub; and
wherein a depth of the distal portion of said bore is sufficient to enable the body to rigidly connect to the cylindrical needle hub of the hollow needle without requiring additional support.

2. The after-loader device of claim 1, further comprising:
a radiation shield configured to slide over an outer circumferential surface of a main portion of said body, to thereby cover the main portion of said body.

3. The after-loader device of claim 2, wherein said body is translucent or transparent so that a user can observe an implant loaded into said bore, when said radiation shield is at least partially removed.

4. The after-loader device of claim 2, wherein:
a distal portion of said body has an outer diameter that is greater than an outer diameter of said main portion of the body, and greater than an inner diameter of said radiation shield;
wherein said distal portion of said body provides a stop for the radiation shield, and also accommodates said distal portion of said bore.

5. The after-loader device of claim 4, further comprising:
a tapered outer circumference extending between said distal portion of said body and said main portion of said body;
wherein said tapered outer circumference provides for a friction fit between said body and said radiation shield.

6. The after-loader device of claim 1, further comprising:
a distal end plug to plug a distal opening of said bore; and
a proximal end plug to plug a proximal opening of said bore;
wherein said distal end plug and said proximal end plug, when respectively plugged into said distal and proximal openings of said bore, prevent an implant loaded in said bore from falling out of said bore.

7. The after-loader device of claim 6, wherein each said end plug includes a gripping portion and an insertion portion.

8. The after-loader device of claim 6, wherein said end plugs are made from a radiation blocking material.

9. The after-loader device of claim 1, wherein a proximal portion of said bore is funneled to assist with inserting an implant and/or a stylet into said bore.

10. The after-loader device of claim 1, further comprising a tapered nose at said distal end of said body, said tapered nose configured to fit into a hub of a second type of hollow needle.

11. The after-loader device of claim 1, further comprising an adapter for use in connecting said body of the after-loader device to a second type of hollow needle.

12. The after-loader device of claim 11, wherein said adaptor includes:
a central portion;
a distal hollow shaft; and
a proximal hollow shaft;
wherein said distal hollow shaft is for insertion into a hub of the second type of needle and into a proximal most portion of a lumen of the second type of needle; and
wherein said proximal hollow shaft is for insertion into said distal portion of said bore of said body of the after-loader device.

13. The after-loader device of claim 12, wherein said central portion of said adaptor includes inner threads for engaging threads on the hub of the second type of needle.

14. An after-loader device useful for loading an implant into a hollow needle after the needle is inserted into patient tissue, the after-loader device comprising:
an elongated body including distal portion and a main portion; and
a bore that extends axially through said body;
wherein a distal portion of said bore, which extends through said distal portion of said body, is configured to receive, and thereby connect to, a cylindrical needle hub of a hollow needle; and
wherein a depth of said distal portion of said bore is sufficient to enable said body to rigidly connect to a cylindrical needle hub of a hollow needle without requiring additional support.

15. The after-loader device of claim 14, further comprising:
a radiation shield configured to slide over an outer circumferential surface of said main portion of said body, to thereby cover said main portion of said body.

16. The after-loader device of claim 15, wherein said body is translucent or transparent so that a user can observe an implant loaded into said bore, when said radiation shield is at least partially removed.

17. The after-loader device of claim 15, wherein:
a distal portion of said body has an outer diameter that is greater than an outer diameter of said main portion of the body, and greater than an inner diameter of said radiation shield;
wherein said distal portion of said body provides a stop for the radiation shield, and also accommodates said distal portion of said bore.

18. The after-loader device of claim 17, further comprising:
a tapered outer circumference extending between said distal portion of said body and said main portion of said body;
wherein said tapered outer circumference provides for a friction fit between said body and said radiation shield.

19. The after-loader device of claim 14, further comprising:
a distal end plug to plug a distal opening of said bore; and
a proximal end plug to plug a proximal opening of said bore;
wherein said distal end plug and said proximal end plug, when respectively plugged into said distal and proximal openings of said bore, prevent an implant loaded in said bore from falling out of said bore.

20. The after-loader device of claim 14, wherein a proximal portion of said body includes a proximal portion of said bore, which is funneled to assist with inserting an implant and/or a stylet into said bore.

21. A brachytherapy kit, comprising:
a plurality of after-loader devices, each of which is useful for loading an implant into a hollow needle after the needle is inserted into patient tissue; and
a plurality of treatment members, each said member including a plurality of radioactive sources spaced apart from one another;
wherein each said member is loaded into a bore of one of said after-loader devices, and maintained in said bore by end-plugs or by friction between the member and said bore
wherein for each said after-loader device:
said elongated body includes proximal portion and a main portion; and
said bore extends axially through said body;
a distal portion of said bore, which extends through a distal portion of said body, is configured to receive, and thereby connect to, a cylindrical needle hub of a hollow needle; and
wherein a depth of said distal portion of said bore is sufficient to enable said body to rigidly connect to a cylindrical needle hub of a hollow needle without requiring additional support.

22. The kit of claim 21, wherein each said after-loader device includes a radiation shield that surrounds at a main portion of an elongated body of said after-loader device.

23. The kit of claim 21, further comprising:
at least one stylet having a length that is at least as long as a total length of a said after-loader device connected with a hollow needle.

24. The kit of claim 23, further comprising:
a least one hollow needle.

25. The kit of claim 21, wherein the plurality of treatment members fulfill an entire predetermined treatment plan for a patient.

26. The kit of claim 25, wherein said radiations sources in said treatment members are spaced apart from on another in accordance with the treatment plan.

27. The kit of claim 25, further comprising:
a tray holding said plurality of after-loader devices loaded with said plurality of treatment members; and
a pouch housing said tray, which is holding said plurality of after-loader devices loaded with said plurality of treatment members, wherein said pouch keeps its contents sterile until said pouch is opened.

28. A brachytherapy kit, comprising;
a plurality of after-loader devices, each of which is useful for loading an implant into a hollow needle after the needle is inserted into patient tissue; and
a plurality of treatment members, each said member including a plurality of radioactive sources spaced apart from one another;
wherein each said member is loaded into a bore of one of said after-loader devices, and maintained in said bore by end-plugs or by friction between the member and said bore; and
at least one adaptor configured to connect a said after-loader device to a second type of hollow needle.

29. The kit of claim 28, further comprising:
at least one second type of hollow needle.

* * * * *